US00PP37201P2

(12) United States Plant Patent
Koot

(10) Patent No.: US PP37,201 P2
(45) Date of Patent: Jan. 6, 2026

(54) ***PETUNIA* PLANT NAMED 'Dopetpotyel 25'**

(50) Latin Name: ***Petunia* X *hybrida***
Varietal Denomination: Dopetpotyel 25

(71) Applicant: DUMMEN GROUP B.V., De Lier (NL)

(72) Inventor: Arjan Koot, Oeffelt (NL)

(73) Assignee: DÜMMEN GROUP B.V., De Lier (NL)

( * ) Notice: Subject to any disclaimer, the term of this patent is extended or adjusted under 35 U.S.C. 154(b) by 0 days.

(21) Appl. No.: 19/054,359

(22) Filed: Feb. 14, 2025

(51) Int. Cl.
*A01H 5/02* (2018.01)
*A01H 6/82* (2018.01)

(52) U.S. Cl.
USPC ..... Plt./356.13
CPC ..... *A01H 6/824* (2018.05); *A01H 5/02* (2013.01)

(58) Field of Classification Search
USPC ..... Plt./356.13, 1, 356.1
CPC . A01H 5/02; A01H 5/00; A01H 6/824; A01H 6/82
See application file for complete search history.

(56) References Cited

U.S. PATENT DOCUMENTS

PP34,342 P2 * 6/2022 Danziger ..... Plt./356.1

OTHER PUBLICATIONS

Dummen Orange Potunia Yellow 2025 retrieved on Apr. 30, 2025 at https://na.dummenorange.com/app/en/products/netherlands/petunia/potunia-yellow-2025-(intrinsa)/PAT_39211, 3 pp. (Year: 2025).*
Issuu Dummen Orange 24-25 Annuals 2024, retrieved on Apr. 30, 2025 at https://issuu.com/bepplerkft/docs/dummen_muskatli_balkon_katalogus_2024-25, pp. 1-3,10,13,132-133. (Year: 2024).*
RHS *Petunia* Capella Hello Yellow, retrieved on Apr. 30, 2025 at https://www.rhs.org.uk/plants/525962/petunia-capella-hello-yellow-(-dpethloylw-)-(capella-series)/details, 3 pp. (Year: 2025).*

* cited by examiner

*Primary Examiner* — June Hwu
(74) *Attorney, Agent, or Firm* — C. Anne Whealy

(57) ABSTRACT

A new and distinct cultivar of *Petunia* plant named 'Dopetpotyel 25', characterized by its relatively compact, semi-upright and uniformly mounding plant habit; relatively moderately vigorous growth habit and moderate growth rate; freely branching habit; early and freely flowering habit; light yellow green-colored flowers with large greenish yellow-colored centers; good container and garden performance; and resistance to Tobacco Mosaic Virus.

1 Drawing Sheet

Botanical designation: *Petunia* X *hybrida*.
Cultivar denomination: 'DOPETPOTYEL 25'.

CROSS REFERENCED TO CLOSELY-RELATED APPLICATION

A European Community Plant Breeder's Rights application for the instant plant was filed by the Applicant/Assignee, Dümmen Group B.V. of De Lier, The Netherlands on Oct. 11, 2024, application number 2024/2370 and published on Dec. 15, 2024. Foreign priority is not claimed to this application.

BACKGROUND OF THE INVENTION

The present invention relates to a new and distinct cultivar of *Petunia* plant, botanically known as *Petunia* X *hybrida* and hereinafter referred to by the name 'Dopetpotyel 25'.

The new *Petunia* plant is a product of a planned breeding program conducted by the Inventor in Rheinberg, Germany. The objective of the breeding program is to create new compact, freely branching and early-flowering *Petunia* plants with numerous attractive flowers.

The new *Petunia* plant originated from a cross-pollination made by the Inventor in July 2021 in Rheinberg, Germany of a proprietary selection of *Petunia* X *hybrida* identified as code number TT21-K0461, not patented, as the female, or seed, parent with a proprietary selection of *Petunia* X *hybrida* identified as code number TT21-K0397, not patented, as the male, or pollen, parent. The new *Petunia* plant was discovered and selected by the Inventor as a single flowering plant from within the progeny of the stated cross-pollination in a controlled greenhouse environment in Rheinberg, Germany in April 2022.

Asexual reproduction of the new *Petunia* plant by terminal vegetative cuttings in a controlled greenhouse environment in Rheinberg, Germany since April 2022 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dopetpotyel 25'. These characteristics in combination distinguish 'Dopetpotyel 25' as a new and distinct *Petunia* plant:

1. Relatively compact, semi-upright and uniformly mounding plant habit.

2. Relatively moderately vigorous growth habit and moderate growth rate.
3. Freely branching habit.
4. Early and freely flowering habit.
5. Light yellow green-colored flowers with large greenish yellow-colored centers.
6. Good container and garden performance.
7. Resistant to Tobacco Mosaic Virus.

Plants of the new *Petunia* can be compared to plants of the female parent selection. In side-by-side comparisons, plants of the new *Petunia* differ primarily from plants of the female parent selection in the following characteristics:

1. Plants of the new *Petunia* are more compact than plants of the female parent selection.
2. Plants of the new *Petunia* are more freely branching than plants of the female parent selection.
3. Plants of the new *Petunia* have healthier leaves than plants of the female parent selection.
4. Plants of the new *Petunia* are more tolerant to high production temperatures than plants of the female parent selection.

Plants of the new *Petunia* can be compared to plants of the male parent selection. In side-by-side comparisons, plants of the new *Petunia* differ primarily from plants of the male parent selection in the following characteristics:

1. Plants of the new *Petunia* are more compact than plants of the male parent selection.
2. Plants of the new *Petunia* are more freely branching than plants of the male parent selection.
3. Plants of the new *Petunia* have larger flowers than plants of the male parent selection.

Plants of the new *Petunia* can be compared to plants of *Petunia* X *hybrida* 'Dpethloylw', disclosed in U.S. Plant Pat. No. 34,342. In side-by-side comparisons, plants of the new *Petunia* and 'Dpethloylw' differ primarily in the following characteristics:

1. Plants of the new *Petunia* are more compact than plants of 'Dpethloylw'.
2. Plants of the new *Petunia* have shorter internodes than plants of 'Dpethloylw' giving a denser appearance.
3. Flowers of plants of the new *Petunia* are light yellow green in color with large greenish yellow-colored centers whereas flowers of plants of 'Dpethloylw' are solid greenish yellow in color.
4. Plants of the new *Petunia* are resistant to Tobacco Mosaic Virus whereas plants of 'Dpethloylw' are not resistant to Tobacco Mosaic Virus.

BRIEF DESCRIPTION OF THE PHOTOGRAPH

The accompanying colored photograph illustrates the overall appearance of the new *Petunia* plant showing the colors as true as it is reasonably possible to obtain in colored reproductions of this type. Colors in the photograph may differ slightly from the color values cited in the detailed botanical description which accurately describe the colors of the new *Petunia* plant.

The photograph is a side perspective view of a typical flowering plant of 'Dopetpotyel 25' grown in a container.

DETAILED BOTANICAL DESCRIPTION

The aforementioned photograph and following observations, measurements and values describe plants grown during the spring and summer in 22-cm containers in a glass-covered greenhouse in Rheinberg, Germany and under cultural practices typical of commercial *Petunia* production. During the production of the plants, day and night temperatures averaged 18° C. and light levels averaged 4,500 lux. Plants were twelve weeks from planting rooted young plants when the photograph was taken and 25 weeks from planting rooted young plants when the description was taken. In the following description, color references are made to The Royal Horticultural Society Colour Chart, Fifth Edition, except where general terms of ordinary dictionary significance are used.

Botanical classification: *Petunia* X *hybrida* 'Dopetpotyel 25'.

Parentage:

*Female, or seed, parent.*—Proprietary selection of *Petunia* X *hybrida* identified as code number TT21-K0461, not patented.

*Male, or pollen, parent.*—Proprietary selection of *Petunia* X *hybrida* identified as code number TT21-K0397, not patented.

Propagation:

*Type.*—By terminal vegetative cuttings.

*Time to initiate roots, summer.*—About five days at temperatures about 20° C.

*Time to initiate roots, winter.*—About seven days at temperatures about 20° C.

*Time to produce a rooted young plant, summer.*—About three weeks at temperatures about 20° C.

*Time to produce a rooted young plant, winter.*—About four weeks at temperatures about 20° C.

*Root description.*—Fine, fibrous; close to 155B in color, actual color of the roots is dependent on substrate composition, water quality, fertilizers, substrate temperature and age of roots.

*Rooting habit.*—Freely branching; dense.

Plant description:

*Plant and growth habit.*—Relatively compact, semi-upright and uniformly mounding plant habit; freely branching habit with about nine primary lateral branches each with about ten secondary branches developing after pinching; relatively moderately vigorous growth habit and moderate growth rate.

*Plant height, soil level to top of foliar plane.*—About 15 cm.

*Plant height, soil level to top of floral plane.*—About 19.2 cm.

*Plant diameter.*—About 44.3 cm.

Lateral branch description:

*Length.*—About 21 cm.

*Diameter.*—About 5 mm.

*Internode length.*—About 1.1 cm.

*Strength.*—Moderately strong.

*Aspect.*—Initially upright to somewhat outwardly spreading to eventually trailing.

*Texture and luster.*—Pubescent; semi-glossy.

*Color, developing.*—Close to 144A.

*Color, developed.*—Close to 145A; at the internodes, close to 144B.

Leaf description:

*Arrangement.*—Before flowering, alternate; after flowering, opposite; simple.

*Length.*—About 5.1 cm.

*Width.*—About 2.9 cm.

*Shape.*—Spatulate.

*Apex.*—Obtuse.

*Base.*—Attenuate.

*Margin*.—Entire.

*Texture and luster, upper and lower surfaces*.—Pubescent; leathery; semi-glossy.

*Venation pattern*.—Pinnate; arcuate.

*Color*.—Developing leaves, upper and lower surfaces: Close to 144A. Fully expanded leaves, upper surface: Close to 146A; venation, close to 144B. Fully expanded leaves, lower surface: Close to 146B; venation, close to 144A.

*Petioles*.—Length: About 1.5 cm. Diameter: About 3.4 mm. Strength: Moderately strong; firm. Texture and luster, upper and lower surfaces: Smooth, glabrous; matte. Color, upper surface: Close to 144A. Color, lower surface: Close to 144B.

Flower description:

*Flower type and flowering habit*.—Single salverform flowers arising from leaf axils; freely flowering habit with usually about 144 flowers and flower buds developing per plant during the flowering season; flowers face mostly upright to somewhat outwardly.

*Fragrance*.—None detected.

*Natural flowering season*.—Plants flower continuously during the spring and summer in Germany; early flowering habit, plants typically beginning flowering about nine weeks after planting.

*Flower longevity*.—Depending on temperature and light levels, individual flowers last about two to six days on the plant; flowers persistent.

*Flower buds*.—Length: About 4 cm. Diameter: About 6.6 mm. Shape: Ovoid. Texture and luster: Rippled; semi-glossy. Color: Close to 145A.

*Flower diameter*.—About 5.5 cm by 6.5 cm.

*Flower depth* (*height*).—About 5.1 cm.

*Flower throat diameter*.—About 1.3 cm.

*Flower tube length*.—About 3 cm.

*Flower tube diameter, proximally*.—About 9.4 mm.

*Corolla*.—Arrangement: Five petals fused at the base and opening into a flared trumpet medium lobing. Petal lobe length (from throat): About 2.8 cm. Petal lobe width: About 2.9 cm. Petal shape: Roughly spatulate. Petal apex: Obtuse. Petal margin: Entire; slightly undulate. Petal texture and luster, upper and lower surfaces: Rugose, glabrous; semi-glossy. Throat texture and luster: Rugose, glabrous; semi-glossy. Tube texture and luster: Rugose, glabrous; semi-glossy. Color: Petal lobe, when opening, upper surface: Close to 151B; towards the margins, close to 145C to 145D. Petal lobe, when opening, lower surface: Close to N144D. Petal lobe, fully opened, upper surface: Close to 151B to 151C; towards the margins, close to 154D; venation, moderately conspicuous and close to 151B; colors do not change with subsequent development. Petal lobe, fully opened, lower surface: Close to 154C to 154D; venation, moderately conspicuous and close to 145A; colors do not change with subsequent development. Flower throat: Close to 151B; venation, close to 151A. Flower tube: Close to 145B; venation, close to 145A.

*Sepals*.—Arrangement: Five sepals fused at the base forming a tubular star-shaped calyx. Length: About 1.7 cm. Diameter: About 5.2 mm. Shape: Oblong. Apex: Rounded. Base: Decurrent. Margin: Entire. Texture and luster, upper and lower surfaces: Smooth, glabrous; semi-glossy. Color: When opening and fully opened, upper surface: Close to 146A. When opening and fully opened, lower surface: Close to 146B.

*Peduncles*.—Length: About 4.3 cm. Diameter: About 2 mm. Strength: Moderately strong. Texture and luster: Smooth, glabrous; semi-glossy. Color: Close to 137C.

*Reproductive organs*.—Stamens: Quantity per flower: Five. Filament length: About 1.1 cm. Filament color: Close to 145D. Anther size: About 1 mm by 2 mm. Anther shape: Ovate. Anther color: Close to 162B. Pollen amount: Abundant. Pollen color: Close to 11C. Pistils: Quantity per flower: One. Pistil length: About 2.1 cm. Style length: About 2 cm. Style color: Close to 145B. Stigma diameter: About 2 mm. Stigma shape: Rounded. Stigma color: Close to 143B. Ovary color: Close to 143C. Fruits: Quantity produced per plant: About 24 during the flowering season. Length: About 5 mm. Diameter: About 3 mm. Texture: Smooth, glabrous. Color: Close to 144B. Seeds: Quantity per flower: About 24. Length: About 0.5 mm. Diameter: About 0.5 mm. Texture: Smooth, glabrous. Color: Close to 163B.

Garden performance: Plants of the new *Petunia* have been observed to have good garden performance and tolerate wind, rain, temperatures ranging from about 3° C. to about 28° C. and to be suitable for USDA Hardiness Zone 11.

Pathogen resistance: Plants of the new *Petunia* have been observed to be resistant to Tobacco Mosaic Virus. To date, plants of the new *Petunia* have not been observed to be resistant to other pathogens common to *Petunia* plants.

It is claimed:

1. A new and distinct *Petunia* plant named 'Dopetpotyel 25' as herein illustrated and described.

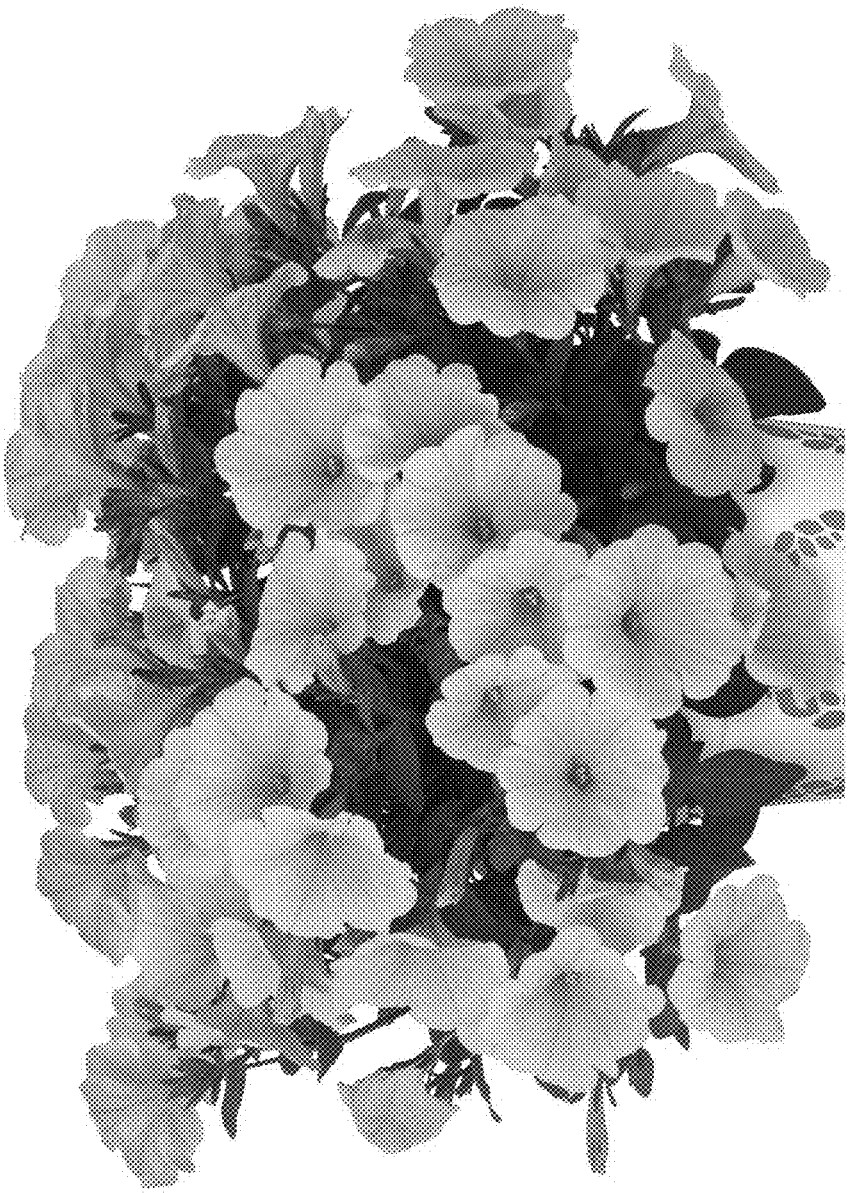

* * * * *